(12) United States Patent
Yoo et al.

(10) Patent No.: US 10,106,622 B2
(45) Date of Patent: Oct. 23, 2018

(54) HUMAN ANTIBODY SPECIFIC TO C-MET AND PREPARATION METHOD THEREOF

(71) Applicant: PHARMABCINE INC., Daejeon (KR)

(72) Inventors: Jinsang Yoo, Daejeon (KR); Ju Ryoung Nam, Daejeon (KR); Jin San Yoo, Daejeon (KR); Sung-Woo Kim, Daejeon (KR); Weon Sup Lee, Daejeon (KR); Sang Ryeol Shim, Daejeon (KR); Sang Soon Byun, Daejeon (KR); Miju Park, Daejeon (KR); Hyuk Joon Lee, Daejeon (KR); Do Yun Kim, Chungcheongbuk-do (KR); Yeon Ju Kim, Daejeon (KR); Mi Ae Jeon, Daejeon (KR); Jinhee Choi, Daejeon (KR); Youngae Lee, Daejeon (KR); Kyoung Hee Nahm, Daejeon (KR); Boyoung Jeong, Daejeon (KR); Seon Young Lee, Seoul (KR); Jong Geun Jeong, Daejeon (KR); Jae Bong Yoon, Daejeon (KR); Nam Ye Kim, Daejeon (KR); Seon Hwan Oh, Daejeon (KR); Eun Hee Lee, Daejeon (KR); Ji Hye Jeong, Daejeon (KR)

(73) Assignee: PHARMABCINE INC., Daejeon (KR)

( * ) Notice: Subject to any disclaimer, the term of this patent is extended or adjusted under 35 U.S.C. 154(b) by 0 days.

(21) Appl. No.: 15/501,843

(22) PCT Filed: Jul. 28, 2015

(86) PCT No.: PCT/KR2015/007899
§ 371 (c)(1),
(2) Date: Feb. 5, 2017

(87) PCT Pub. No.: WO2016/021864
PCT Pub. Date: Feb. 11, 2016

(65) Prior Publication Data
US 2017/0233492 A1    Aug. 17, 2017

(30) Foreign Application Priority Data

Aug. 7, 2014 (KR) .......................... 10-2014-010557

(51) Int. Cl.
*A61K 39/00* (2006.01)
*C07K 16/32* (2006.01)

(52) U.S. Cl.
CPC ........ *C07K 16/32* (2013.01); *A61K 2039/505* (2013.01); *C07K 2317/622* (2013.01)

(58) Field of Classification Search
CPC .............................................. A61K 2039/505
See application file for complete search history.

(56) References Cited

U.S. PATENT DOCUMENTS

| 6,172,197 | B1 | 1/2001 | McCafferty et al. |
| 7,063,943 | B1 | 6/2006 | McCafferty et al. |
| 2013/0129731 | A1 | 5/2013 | Kim et al. |
| 2014/0193431 | A1 | 7/2014 | Park et al. |

FOREIGN PATENT DOCUMENTS

| JP | 2013-534515 A | 9/2013 |
| KR | 10-0883430 B1 | 2/2009 |
| KR | 10-2012-0134938 A | 12/2012 |
| KR | 10-2013-0059114 A | 6/2013 |
| WO | WO2005016382 A1 | 2/2005 |
| WO | WO2011150454 A1 | 8/2011 |
| WO | WO2011110642 A2 | 9/2011 |
| WO | 2011151412 A1 | 12/2011 |

OTHER PUBLICATIONS

Hall et al. (Immunotechnology. Oct. 1998; 4 (2): 127-40).*
Rudikoff et al. (Proc. Natl. Acad. Sci. USA. 1982; 79: 1979-1983).*
Mariuzza et al. (Annu. Rev. Biophys. Biophys. Chem. 1987; 16: 139-159).*
Gussow et al. (Methods in Enzymology. 1991; 203: 99-121).*
Winkler et al. (J. Immunol. Oct. 15, 2000; 165 (8): 4505-4514).*
Giusti et al. (Proc. Natl. Acad. Sci. USA. May 1987; 84 (9): 2926-2930).*
Chien et al. (Proc. Natl. Acad. Sci. USA. Jul. 1989; 86 (14): 5532-5536).*
Caldas et al. (Mol. Immunol. May 2003; 39 (15): 941-952).*
Vajdos et al. (J. Mol. Biol. Jul. 5, 2002; 320 (2): 415-428).*
De Pascalis et al. (J. Immunol. 2002; 169 (6): 3076-3084).*
Casset et al. (Biochem. Biophys. Res. Commun. Jul. 18, 2003; 307 (1): 198-205).*
Wu et al. (J. Mol. Biol. Nov. 19, 1999; 294 (1): 151-162).*
MacCallum et al. (J. Mol. Biol. Oct. 11, 1996; 262 (5): 732-745).*
Holm et al. (Mol. Immunol. Feb. 2007; 44 (6): 1075-1084).*
Yu et al. (PLoS One. 2012; 7 (3): e33340; pp. 1-15).*
Chang et al. (Structure. Jan. 7, 2014; 22 (1): 9-21).*
Amicone, L, et al., "Transgenic expression in the liver of truncated Met blocks apoptosis and permits immortalization of hepatocytes", "The EMBO Journal", 1997, pp. 495-503, vol. 16, No. 3.

(Continued)

*Primary Examiner* — Stephen L Rawlings
(74) *Attorney, Agent, or Firm* — Hultquist, PLLC; Steven J. Hultquist

(57) ABSTRACT

Provided are an antibody specifically bound to c-Met (c-Met-specific antibody) or fragments thereof, and more specifically, a fully human antibody having high affinity and specificity to c-Met isolated from human Fv(ScFv) phage library, a polynucleotide encoding the antibody, a recombinant vector containing the polynucleotide, a cell transformed with the recombinant vector, and a method of producing the c-Met-specific antibody by culturing the cell, wherein the c-Met-specific antibody may effectively control activity of c-Met in vivo.

8 Claims, 6 Drawing Sheets
(6 of 6 Drawing Sheet(s) Filed in Color)
Specification includes a Sequence Listing.

(56) References Cited

OTHER PUBLICATIONS

Berthou, S., et al., "The Met kinase inhibitor SU11274 exhibits a selective inhibition pattern toward different receptor mutated variants", "Oncogene", Apr. 5, 2004, pp. 5387-5393, vol. 23, Publisher: Nature Publishing Group.

Bhardwaj, V., et al., "Modulation of c-Met signaling and cellular sensitivity to radiation: potential implications for therapy", "Cancer", May 15, 2013, pp. 1769-1775, vol. 119, No. 10.

Burgess, T., et al., "Fully Human Monoclonal Antibodies to Hepatocyte Growth Factor with Therapeutic Potential against Hepatocyte Growth Factor/c-MetDependent Human Tumors", "Cancer Research", Feb. 1, 2006, pp. 1721-1729, vol. 66, No. 3.

Cao, B., et al., "Neutralizing monoclonal antibodies to hepatocyte growth factoryscatter factor (HGFySF) display antitumor activity in animal models", "PNAS", Jun. 19, 2001, pp. 7743-7448, vol. 98, No. 13.

Christensen, J.G., et al., "A Selective Small Molecule Inhibitor of c-Met Kinase Inhibits c-Met-Dependent Phenotypes in Vitro and Exhibits Cytoreductive Antitumor Activity in Vivo", "Cancer Research", Nov. 1, 2003, pp. 7345-7355, vol. 63.

Corps, A.N., et al., "Hepatocyte Growth Factor Stimulates Motility, Chemotaxis and Mitogenesis in Ovarian Carcinoma Cells Expressing High Levels of c-Met", "International Journal of Cancer", 1997, pp. 151-155, vol. 73.

Dean, M., et al., "The human met oncogene is related to the tyrosine kinase oncogenes", "Nature", Nov. 28, 1985, pp. 385-388, vol. 318.

Deuscher, M.P., "Book Reviews: Pure thinking about proteins", "Tibtech", Feb. 1991, p. 69, vol. 9.

Ebert, M., et al., "Coexpression of the c-met Proto-oncogene and Hepatocyte Growth Factor in Human Pancreatic Cancer", "Cancer Research", Nov. 15, 1994, pp. 5775-5778, vol. 54.

Eder, J.P., et al., "NovelTherapeutic Inhibitors of the c-Met Signaling Pathway in Cancer", "Clinical Cancer Research", Apr. 1, 2009, pp. 2207-2214, vol. 15, No. 7.

Edwardraja, S., et al., "Redesigning of Anti-c-Met Single Chain Fv Antibody for the Cytoplasmic Folding and Its Structural Analysis", "Biotechnology and Bioengineering", Feb. 22, 2010, vol. 106, No. 3.

Engelman, J.A., et al., "MET Amplification Leads to Gefitinib Resistance in Lung Cancer by Activating ERBB3 Signaling", "Science", May 18, 2007, pp. 1039-1043, vol. 316.

Harvey, P., et al., "Immunoreactivity for Hepatocyte Growth Factorkcatter Factor and Its Receptor, met, in Human Lung Carcinomas and Malignant Mesotheliomas", "Journal of Pathology", Jun. 6, 1996, pp. 389-394, vol. 180.

Hawkins, R.E., et al., "Selection of Phage Antibodies by Binding Affinity Mimicking Affinity Maturation", "Journal of Molecular Biology", Apr. 10, 1992, pp. 889-896, vol. 226.

Hiscox, S.E., et al., "Expression of the HGF/SF Receptor, c-met, and Its Ligand in Human Colorectal Cancers", "Cancer Investigation", 1997, pp. 513-521, vol. 15, No. 6.

Jeffers, M., et al., "Hepatocyte growth factor/scatter factorMet signaling in tumorigenicity and invasion/metastasis", "Journal of Molecular Medicine", May 28, 2006, pp. 505-513, vol. 74.

Jones, E.W., "Proteinase Mutants of *Saccharomyces cerevisiae*", "Genetics", Jan. 1977, pp. 23-33, vol. 85.

Kim, K.J., et al., "Systemic Anti-Hepatocyte Growth Factor Monoclonal Antibody Therapy Induces the Regression of Intracranial Glioma Xenografts", "Clinical Cancer Research", Feb. 15, 2006, pp. 1292-1298, vol. 12, No. 4.

Kim, K., et al., "A neutralizable epitope is induced on HGF upon its interaction with its receptor cMet", "Biochemical and Biophysical Research Communications", 2007, pp. 115-121, vol. 354.

Kingsman, A.J., et al., "Replication in *Saccharomyces cererisiae* of Plasmid pBR313 Carrying DNA From the Yeast trpl Region", "Gene", Jul. 3, 1979, pp. 141-152, vol. 7.

Klominek, J., et al., "Hepatocyte Growth Factor/Scatter Factor Stimulates Chemotaxis and Growth of Malignant Mesothelioma Cells Through c-met Receptor", "International Journal of Cancer", 1998, pp. 240-249, vol. 76.

Koochekpour, S., et al., "Met and Hepatocyte Growth Factor/Scatter Factor Expression in Human Gliomas", "Cancer Research", Dec. 1, 1997, pp. 5391-5398, vol. 57.

Lamoyi, E., et al., "Preparation of F(ab')2 Fragments from Mouse IgG of Various Subclasses", "Journal of Immunological Methods", 1983, pp. 235-243, vol. 56.

Low, N.M., et al., "Mimicking Somatic Hypermutation: Affinity Maturation of Antibodies Displayed on Bacteriophage Using a Bacterial Mutator Strain", "Journal of Molecular Biology", 1996, pp. 359-368, vol. 260.

Maggiora, P., et al., "Control of Invasive Growth by the HGF Receptor Family", "Journal of Cellular Physiology", 1997, pp. 183-186, vol. 173.

Matsumoto, K., et al., "Hepatocyte Growth Factor (HGF) as a Tissue Organizer for Organogenesis and Regeneration", "Biomedical and Biophysical Research Communications", Sep. 22, 1997, pp. 639-644, vol. 239.

Matsumoto, K., et al., "NK4 (HGF-antagonist/angiogenesis inhibitor) in cancer biology and therapeutics", "Cancer Sci", Apr. 2003, pp. 321-327, vol. 94, No. 4.

Mazzone, M., et al., "An uncleavable form of proscatter factor suppresses tumor growth and dissemination in mice", "The Journal of Clinical Investigation", Nov. 2004, pp. 1418-1432, vol. 114, No. 10.

Morotti, A., et al., "K252a inhibits the oncogenic properties of Met, the HGF receptor", "Oncogene", Apr. 26, 2002, pp. 4885-4893, vol. 21.

Nagy, J., et al., "Expression and Loss of Heterozygosity of c-met Proto-Oncogene in Primary Breast Cancer", "Journal of Surgical Oncology", May 25, 1995, pp. 95-99, vol. 60.

Nagy, J., et al., "Hepatocyte growth factor/scatter factor expression and c-met in primary breast cancer", "Surgical Oncology", 1996, pp. 15-21, vol. 5.

Natali, P.G., et al., "Overexpression of the met/HGF Receptor in Renal Cell Carcinomas", "International Journal of Cancer (Pred. Oncol.)", 1996, pp. 212-217, vol. 69.

Parham, P., "On the fragmentation of monoclonal IgG1, IgG2a, and IgG2b from BALB/c mice", "The Journal of Immunology", Dec. 1983, pp. 2895-2902, vol. 131, No. 6.

Park, M., et al., "Sequence of MET protooncogene cDNA has features characteristic of the tyrosine kinase family of growth-factor receptors", "Proc. Natl. Acad. Sci. USA", Sep. 1987, pp. 6379-6383, vol. 84.

Smith, D.B., et al., "Single-step purification of polypeptides expressed in *Escherichia coli* as fusions with glutathione S-transferase", "Gene", 1988, pp. 31-40, vol. 67.

Stinchcomb, D.T., et al., "Isolation and characterisation of a yeast chromosomal replicator", "Nature", Nov. 1, 1979, pp. 39-43, vol. 282.

Suzuki, K., et al., "Expression of the c-met Protooncogene in Human Hepatocellular Carcinoma", "Heptology", May 29, 1994, pp. 1231-1236, vol. 20, No. 5.

Taniguchi, K., et al., "The Relation between the Growth Patterns of Gastric Carcinoma and the Expression of Hepatocyte Growth Factor Receptor (c-met), Autocrine Motility Factor Receptor, and Urokinase-Type Plasminogen Activator Receptor", "Cancer", Jun. 1, 1998, pp. 2112-2122, vol. 82, No. 11.

Tolnay, E., et al., "Hepatocyte growth factor/scatter factor and its receptor c-Met are overexpressed and associated with an increased microvessel density in malignant pleural mesothelioma", "Journal of Cancer Research and Clinical Oncology", 1998, pp. 291-296, vol. 124.

Tuck, A.B., et al., "Coexpression of Hepatocyte Growth Factor and Receptor (Met) in Human Breast Carcinoma", "American Journal of Pathology", Jan. 1996, pp. 225-232, vol. 148, No. 1.

Yang, W-P., et al., "CDR Walking Mutagenesis for the Affinity Maturation of a Potent Human Anti-HIV-1 Antibody into the Picomolar Range", "Journal of Molecular Biology", 1995, pp. 392-403, vol. 254.

(56) References Cited

OTHER PUBLICATIONS

Zhang, Y., et al., "XL-184, a MET, VEGFR-2 and RET kinase inhibitor for the treatment of thyroid cancer, glioblastoma multiforme and NSCLC", "IDrugs", Feb. 2010, pp. 112-121, vol. 13, No. 2.

Zhao, P., et al., "Identification of a Met-Binding Peptide froma Phage Display Library", "Clinical Cancer Research", Oct. 15, 2007, pp. 6049-6055, vol. 13, No. 20.

Note: For the non-patent literature citations that no month of publication is indicated, the year of publication is more than 1 year prior to the effective filing date of the present application.

* cited by examiner

SEQUENCE LISTING

```
<160> NUMBER OF SEQ ID NOS: 12

<210> SEQ ID NO 1
<211> LENGTH: 5
<212> TYPE: PRT
<213> ORGANISM: Artificial Sequence
<220> FEATURE:
<223> OTHER INFORMATION: HCDR1

<400> SEQUENCE: 1

Thr His Trp Ile Thr
1               5

<210> SEQ ID NO 2
<211> LENGTH: 17
<212> TYPE: PRT
<213> ORGANISM: Artificial Sequence
<220> FEATURE:
<223> OTHER INFORMATION: HCDR2
```

<400> SEQUENCE: 2

Thr Ile Asp Pro Thr Asp Ser Tyr Asn Phe Tyr Gly Pro Ser Phe Gln
1               5                   10                  15

Gly

<210> SEQ ID NO 3
<211> LENGTH: 17
<212> TYPE: PRT
<213> ORGANISM: Artificial Sequence
<220> FEATURE:
<223> OTHER INFORMATION: HCDR3

<400> SEQUENCE: 3

Asp Gly Asn Tyr Tyr Asp Ser Arg Gly Tyr Tyr Tyr Asp Thr Phe Asp
1               5                   10                  15

Met

<210> SEQ ID NO 4
<211> LENGTH: 11
<212> TYPE: PRT
<213> ORGANISM: Artificial Sequence
<220> FEATURE:
<223> OTHER INFORMATION: LCDR1

<400> SEQUENCE: 4

Arg Ala Ser Gln Gly Ile Ser Thr Tyr Leu Ala
1               5                   10

<210> SEQ ID NO 5
<211> LENGTH: 7
<212> TYPE: PRT
<213> ORGANISM: Artificial Sequence
<220> FEATURE:
<223> OTHER INFORMATION: LCDR2

<400> SEQUENCE: 5

Ser Ala Ser Thr Leu Glu Ser
1               5

<210> SEQ ID NO 6
<211> LENGTH: 9
<212> TYPE: PRT
<213> ORGANISM: Artificial Sequence
<220> FEATURE:
<223> OTHER INFORMATION: LCDR3

<400> SEQUENCE: 6

Gln Gln Ala Asp Ser Phe Pro Leu Thr
1               5

<210> SEQ ID NO 7
<211> LENGTH: 126
<212> TYPE: PRT
<213> ORGANISM: Artificial Sequence
<220> FEATURE:
<223> OTHER INFORMATION: Heavy chain variable region

<400> SEQUENCE: 7

Gln Val Gln Leu Val Gln Ser Gly Ala Glu Val Lys Lys Pro Gly Glu
1               5                   10                  15

Ser Leu Arg Ile Ser Cys Gln Gly Ser Gly Tyr Ser Phe Pro Thr His
                20                  25                  30

Trp Ile Thr Trp Val Arg Gln Met Pro Gly Lys Gly Leu Glu Trp Met
            35                  40                  45

Gly Thr Ile Asp Pro Thr Asp Ser Tyr Asn Phe Tyr Gly Pro Ser Phe
        50                  55                  60

Gln Gly His Val Thr Ile Ser Ala Asp Ser Ser Ser Thr Ala Tyr
65                  70                  75                  80

Leu Gln Trp Ser Ser Leu Lys Ala Ser Asp Thr Ala Met Tyr Tyr Cys
                85                  90                  95

Ala Arg Asp Gly Asn Tyr Tyr Asp Ser Arg Gly Tyr Tyr Tyr Asp Thr
                100                 105                 110

Phe Asp Met Trp Gly Gln Gly Thr Leu Val Thr Val Ser Ser
            115                 120                 125

<210> SEQ ID NO 8
<211> LENGTH: 115
<212> TYPE: PRT
<213> ORGANISM: Artificial Sequence
<220> FEATURE:
<223> OTHER INFORMATION: Light chain variable region

<400> SEQUENCE: 8

Asp Ile Gln Met Thr Gln Ser Pro Ser Phe Leu Ser Ala Ser Val Gly
1               5                   10                  15

Asp Arg Val Thr Ile Thr Cys Arg Ala Ser Gln Gly Ile Ser Thr Tyr
                20                  25                  30

Leu Ala Trp Tyr Gln Gln Lys Pro Gly Thr Ala Pro Lys Leu Leu Ile
            35                  40                  45

Tyr Ser Ala Ser Thr Leu Glu Ser Gly Val Pro Ser Arg Phe Ser Gly
        50                  55                  60

Ser Gly Ser Gly Thr Asp Phe Thr Leu Thr Ile Ser Ser Leu Gln Pro
65                  70                  75                  80

Glu Asp Ser Ala Thr Tyr Tyr Cys Gln Gln Ala Asp Ser Phe Pro Leu
                85                  90                  95

Thr Phe Gly Gly Gly Thr Lys Val Glu Ile Lys Arg Gly Gly Ala Ser
                100                 105                 110

Leu Val Glu
        115

<210> SEQ ID NO 9
<211> LENGTH: 23
<212> TYPE: PRT
<213> ORGANISM: Artificial Sequence
<220> FEATURE:
<223> OTHER INFORMATION: amino acid linker

<400> SEQUENCE: 9

Gly Leu Gly Gly Leu Gly Gly Gly Ser Gly Gly Gly Ser Gly
1               5                   10                  15

Gly Ser Ser Gly Val Gly Ser
            20

<210> SEQ ID NO 10
<211> LENGTH: 264
<212> TYPE: PRT
<213> ORGANISM: Artificial Sequence
<220> FEATURE:
<223> OTHER INFORMATION: 1E4 ScFv

```
<400> SEQUENCE: 10

Gln Val Gln Leu Val Gln Ser Gly Ala Glu Val Lys Lys Pro Gly Glu
1               5                   10                  15

Ser Leu Arg Ile Ser Cys Gln Gly Ser Gly Tyr Ser Phe Pro Thr His
            20                  25                  30

Trp Ile Thr Trp Val Arg Gln Met Pro Gly Lys Gly Leu Glu Trp Met
        35                  40                  45

Gly Thr Ile Asp Pro Thr Asp Ser Tyr Asn Phe Tyr Gly Pro Ser Phe
    50                  55                  60

Gln Gly His Val Thr Ile Ser Ala Asp Ser Ser Ser Thr Ala Tyr
65                  70                  75                  80

Leu Gln Trp Ser Ser Leu Lys Ala Ser Asp Thr Ala Met Tyr Tyr Cys
                85                  90                  95

Ala Arg Asp Gly Asn Tyr Tyr Asp Ser Arg Gly Tyr Tyr Tyr Asp Thr
            100                 105                 110

Phe Asp Met Trp Gly Gln Gly Thr Leu Val Thr Val Ser Ser Gly Leu
        115                 120                 125

Gly Gly Leu Gly Gly Gly Ser Gly Gly Gly Ser Gly Gly Ser
130                 135                 140

Ser Gly Val Gly Ser Asp Ile Gln Met Thr Gln Ser Pro Ser Phe Leu
145                 150                 155                 160

Ser Ala Ser Val Gly Asp Arg Val Thr Ile Thr Cys Arg Ala Ser Gln
                165                 170                 175

Gly Ile Ser Thr Tyr Leu Ala Trp Tyr Gln Gln Lys Pro Gly Thr Ala
            180                 185                 190

Pro Lys Leu Leu Ile Tyr Ser Ala Ser Thr Leu Glu Ser Gly Val Pro
        195                 200                 205

Ser Arg Phe Ser Gly Ser Gly Ser Gly Thr Asp Phe Thr Leu Thr Ile
        210                 215                 220

Ser Ser Leu Gln Pro Glu Asp Ser Ala Thr Tyr Tyr Cys Gln Gln Ala
225                 230                 235                 240

Asp Ser Phe Pro Leu Thr Phe Gly Gly Gly Thr Lys Val Glu Ile Lys
                245                 250                 255

Arg Gly Gly Ala Ser Leu Val Glu
            260

<210> SEQ ID NO 11
<211> LENGTH: 378
<212> TYPE: DNA
<213> ORGANISM: Artificial Sequence
<220> FEATURE:
<223> OTHER INFORMATION: Heavy chain variable region

<400> SEQUENCE: 11
caggtgcagc tggtgcagtc tggagcagag gtgaaaaagc ccggggagtc tctgaggatc      60
tcctgtcagg gttctggata cagttttccc acccactgga tcacctgggt gcgccagatg     120
cccgggaaag gcctggagtg gatgggaacg attgatccta ctgactctta caatttctat     180
ggaccgtcgt tccaaggcca cgtcaccatc tcagccgaca gctccagcag caccgcctac     240
ctgcagtgga gcagcctgaa ggcctcggac accgccatgt attactgtgc gagagatggc     300
aactactatg atagtcgcgg ttattactac gatactttg atatgtgggg ccaagggaca     360
ctggtcaccg tctcctca                                                    378
```

```
<210> SEQ ID NO 12
<211> LENGTH: 348
<212> TYPE: DNA
<213> ORGANISM: Artificial Sequence
<220> FEATURE:
<223> OTHER INFORMATION: Light chain variable region

<400> SEQUENCE: 12
tccgacatcc agatgaccca gtctccatcc ttcctctctg catctgtcgg agacagagtc       60
accatcactt gccgggccag tcagggcatc agtacttatt tagcctggta tcaacaaaaa      120
ccagggacag cccctaaact cctgatctat tctgcatcca ctttggaaag tggggtccca      180
tcgcgattca gcggaagtgg atccgggaca gatttcactc tcaccatcag cagcctgcag      240
cctgaagatt ctgcaactta ctattgtcaa caggctgaca gtttcccgct cactttcggc      300
ggagggacca aggtggagat caaacgtgga ggagccagcc tcgtggaa                   348
```

HUMAN ANTIBODY SPECIFIC TO C-MET AND PREPARATION METHOD THEREOF

CROSS-REFERENCE TO RELATED APPLICATIONS

This application is a U.S. national phase under the provisions of 35 U.S.C. § 371 of International Patent Application No. PCT/KR15/07899 filed Jul. 28, 2015, which in turn claims priority of Korean Patent Application No. 10-2014-0101557 filed Aug. 7, 2014. The disclosures of such international patent application and Korean priority patent application are hereby incorporated herein by reference in their respective entireties, for all purposes.

TECHNICAL FIELD

The present disclosure relates to an antibody specifically bound to c-Met (hereinafter, referred to as a c-Met-specific antibody) or fragments thereof, and more specifically, to a fully human antibody having high affinity and specificity to c-Met isolated from human Fv(ScFv) phage library, a polynucleotide encoding the antibody, a recombinant vector containing the polynucleotide, a cell transformed with the recombinant vector, and a method of producing the c-Met-specific antibody by culturing the cell.

BACKGROUND ART

It was found that c-Met (mesenchymal-epithelial transition factor) is a receptor on a cell surface and a cancer gene (oncogene) of a receptor tyrosine kinase family, and is configured of alpha (a) sub-unit only consisting of 50 kD of extracellular domains, and beta (β) sub-unit consisting a total of 145 kD of tyrosine motif related with extracellular, cellular membrane permeation, tyrosine kinase domain, and phosphorylation (Dean et al., Nature, 4; 318(6044):385, 1985; Park et al., PNAS, 84(18):6379, 1987, Maggiora et al., J. Cell Physiol., 173:183, 1997). It has been reported that expression of inappropriate c-Met or HGF is related with various types of malignant tumors, and when it is over-expressed, prognosis is not good (www.vai.org/met, Eder et al., Clin. Cancer Res., 15:2207, 2009).

c-Met responds to HGF and stimulates various signal transduction pathways through phosphorylation of c-Met to promote transformation, that is, to promote mitogenesis of tumor cells and blood vessel cells and motility of cells, inhibits cell death, and induces angiogenesis, and invasion and metastasis to an extracellular matrix (ECM), etc. (Jeffers et al., J. Mol. Med., 74:505, 1996; Amicone et al., EMBO J., 16:495, 1997; Matsumoto and Nakamura, Biochem. Biophys. Res. Comm., 239:639, 1997; Corps et al., Int. J. Cancer, 73:151, 1997). In particular, it has been reported that c-Met and HGF are simultaneously over-expressed in various cancer tissues and cells such as glioma (Koochekpour et al., Cancer Res., 57:5391, 1997), breast cancer (Nagy et al., Surg. Oncol., 5:15, 1996; Tuck et al., Am. J. Pathol., 148:225, 1996), pancreatic cancer (Ebert et al., Cancer Res., 54:5775, 1994), pleural mesothelioma (Tolpay et al., J. Cancer Res. Clin. Oncol., 124:291, 1998); (Klominek et al. Intl. J. Cancer, 76: 240, 1998), etc. However, cases in which development into cancer progresses by over-expression of c-Met regardless of HGF, have been frequently observed. For example, there are liver cancer (hepatocellular carcinoma, Suzuki et al., Hepatology, 20 (5): 1231, 1996), gastric cancer (Taniguchi et al., Cancer, 82:2112-2122 (1998)), lung cancer (Harvey et al., J. Pathol, 180: 389, 1996), kidney cancer (Natali et al., Intl. J. Cancer, 69:212, 1996), ovarian cancer (Nagy et al, J. Surg. Oncol, 60:95, 1995), colorectal cancer (Hiscox et al., Cancer Invest., 15:513, 1997), etc., as good examples. When c-Met is activated or over-expressed, transformation is promoted as described above, such that various methods of inhibiting activation of c-Met have been developed as promising anti-cancer therapeutic strategy. As examples thereof, there are low molecular weight compounds which are designed to interfere with binding of ATP (adenosine triphosphate) to c-Met. The low molecular weight compounds include K252a (Fermentek Biotechnology), SU11274 (Sugen), PHA-665752 (Pfiza), etc., (Morotti et al., Oncogene, 21(32):4885, 2002; Berthou et al., Oncogene, 23(31):5387, 2004; Pfizer, Christensen et al., Cancer Res., 63(21):7345, 2003), and these examples were designed to interfere with phosphorylation of c-Met, such that downstream proteins of signal transfer are not activated. However, the low molecular weight compounds have a disadvantage in that they are not capable of specifically inhibiting the phosphorylation by c-Met.

In addition, as a second method of neutralizing the signaling transfer mechanism of HGF/c-Met, there is a method of inhibiting the binding of c-Met and HGF which is a ligand of c-Met. The method of inhibiting the binding of c-Met and HGF includes a method of using lost HGF fragments (Matsumoto & Nakamura, Cancer Sci., 94(4): 321, 2003), antibodies neutralizing HGF (Cao et al., PNAS., 98(13):7443, 2001; Kim et al., Clin. Cancer Res., 12:1292, 2006; Burgess et al., Cancer Res., 66(3):1721, 2006), or HGF precursors (pro-HGF, Mazzone et al., J. Clin. Invest., 114(10):1418, 2004) that do not activate c-Met but are bound to c-Met with stronger affinity than the original HGF. Further, peptide sequences capable of inhibiting activity of c-Met are selected by using a phage display method and panning technique, such that corresponding peptides are used to prevent activation of c-Met (Kim et al., Biochem Biophys Res Commun., 354: 115, 2007). The selected peptides are applied to molecular imaging for searching in vivo tissue or organ in which c-Met is over-expressed (Cao et al., Clin. Cancer Res., 13(20); 6049, 2007). The selected peptides have limitation in that HGF-dependent c-Met activation is only inhibited, but anti-cancer effects are actually shown in vitro or in vivo, such that it is thought that the selected peptides are effectively used through applications such as combining with existing chemotherapy, etc. In addition, gefitinib and erlotinib which are epidermal growth factor receptors (EGFR) kinase inhibitors are used as an effective cancer therapeutic agent, but frequently have drug resistance, and the reason thereof has been reported to be an intense amplification of c-Met receptor (Engelman et al., Science, 316(5827):1039, 2007), and accordingly, it is expected that when c-Met inhibitors are merge-treated, anti-cancer effects are amplified.

Further, it is well known that c-Met is activated by HGF to contribute to angiogenesis by itself, and stimulates angiogenesis throughout interaction with VEGFR-2 which is the major receptor of angiogenesis. Here, it could be observed that when inhibition is achieved by simultaneously targeting c-Met and VEGFR-2, tumor growth is synergistically inhibited in a human xenograft model (Zhang et al., IDrugs, 13:112, 2010).

It is known that dysregulation between HGF and c-Met and over-expression of c-Met play an important role in progression of metastatic cancer, and accordingly, antibody for c-Met has been largely developed as an antagonist in anti-cancer agents.

Therefore, the present inventors made an effort to develop a c-Met human antibody capable of specifically binding to c-Met with high affinity and consisting of human-derived sequences to have a low immune response-induced potential upon in vivo administration, and as a result, separated a fully human antibody bound to c-Met with high affinity and specificity from single-chain Fv(ScFv) phage library by using a phage display method, and completed the present disclosure.

DISCLOSURE

Technical Problem

An object of the present disclosure is to provide a heavy chain variable region of a c-Met-specific antibody having high affinity and specificity to c-Met.

Another object of the present disclosure is to provide a light chain variable region of the c-Met-specific antibody having high affinity and specificity to c-Met.

Still another object of the present disclosure is to provide a c-Met-specific antibody including the heavy chain variable region of the c-Met-specific antibody; and the light chain variable region of the c-Met-specific antibody or fragments thereof.

Still another object of the present disclosure is to provide a polynucleotide encoding the heavy chain variable region of the c-Met-specific antibody or the light chain variable region of the c-Met-specific antibody.

Still another object of the present disclosure is to provide a recombinant vector containing the polynucleotide and a recombinant cell transformed with the recombinant vector.

Still another object of the present disclosure is to provide a method of producing the c-Met-specific antibody using the recombinant cell.

Technical Solution

In order to achieve the foregoing objects, the present disclosure provides a heavy chain variable region of a c-Met-specific antibody including a heavy chain variable region CDR1 represented by an amino acid sequence of SEQ ID NO: 1; a heavy chain variable region CDR2 represented by an amino acid sequence of SEQ ID NO: 2; and a heavy chain variable region CDR3 represented by an amino acid sequence of SEQ ID NO: 3, and preferably, provides a heavy chain variable region of a c-Met-specific antibody having an amino acid sequence of SEQ ID NO: 7.

In addition, the present disclosure provides a light chain variable region of a c-Met-specific antibody including a light chain variable region CDR1 represented by an amino acid sequence of SEQ ID NO: 4; a light chain variable region CDR2 represented by an amino acid sequence of SEQ ID NO: 5; and a light chain variable region CDR3 represented by an amino acid sequence of SEQ ID NO: 6, and preferably, provides a light chain variable region of a c-Met-specific antibody having an amino acid sequence of SEQ ID NO: 8.

Further, the present disclosure provides a c-Met-specific antibody including: a heavy chain variable region of the c-Met-specific antibody including a heavy chain variable region CDR1 represented by an amino acid sequence of SEQ ID NO: 1; a heavy chain variable region CDR2 represented by an amino acid sequence of SEQ ID NO: 2; and a heavy chain variable region CDR3 represented by an amino acid sequence of SEQ ID NO: 3; and a light chain variable region of the c-Met-specific antibody including a light chain variable region CDR1 represented by an amino acid sequence of SEQ ID NO: 4; a light chain variable region CDR2 represented by an amino acid sequence of SEQ ID NO: 5; and a light chain variable region CDR3 represented by an amino acid sequence of SEQ ID NO: 6, or fragments thereof.

The c-Met-specific antibody or the fragments thereof according to the present disclosure may include the heavy chain variable region represented by SEQ ID NO: 7 and the light chain variable region represented by SEQ ID NO: 8.

In addition, the present disclosure provides a polynucleotide encoding the heavy chain variable region of the c-Met-specific antibody or the light chain variable region of the c-Met-specific antibody.

Further, the present disclosure provides a recombinant vector containing the polynucleotide, and a recombinant cell transformed with the recombinant vector.

Further, the present disclosure provides a method of producing a c-Met-specific antibody including producing the c-Met-specific antibody by culturing the recombinant cell; and recovering the produced c-Met-specific antibody.

DESCRIPTION OF DRAWINGS

The patent or application file contains at least one drawing executed in color. Copies of this patent or patent application publication with color drawings will be provided by the Office upon request and payment of the necessary fee.

BEST MODE

Figure 1:
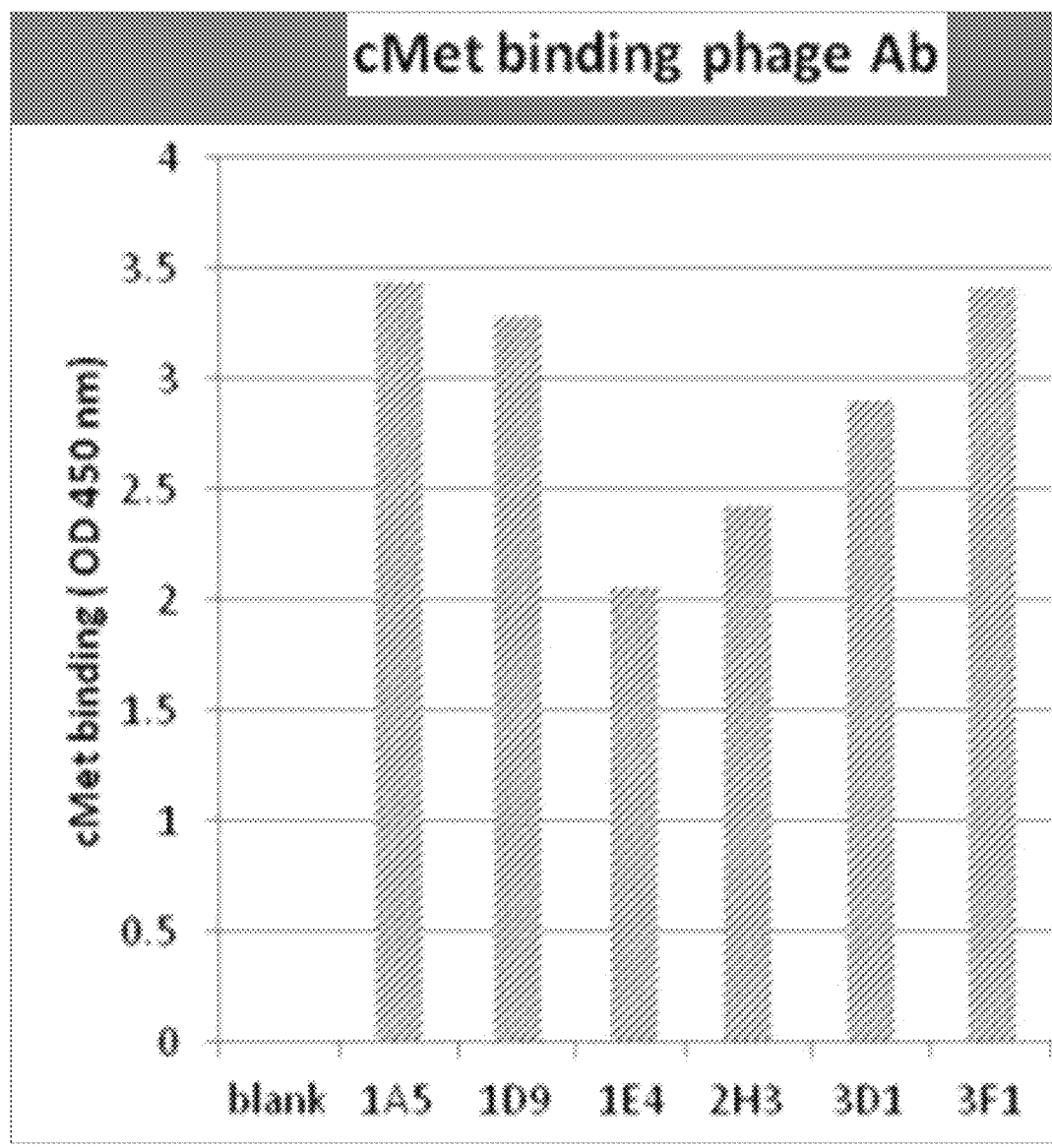
FIG. 1 shows a binding capacity to c-Met, of c-Met-specific ScFv which is screened in the present disclosure.

As far as it is not defined in other ways, all technical and scientific terms used in the present specification have the same meaning as being generally appreciated by those skilled in the art to which the present disclosure pertains. In general, nomenclature used in the present specification and experimental methods to be described below are well known and generally used in the present technical field.

An antibody according to the present disclosure is capable of specifically binding to c-Met with high affinity and consisting of human-derived sequences.

In one aspect of the present disclosure, the present disclosure provides a heavy chain variable region of a c-Met-specific antibody including: a heavy chain variable region CDR1 represented by an amino acid sequence of SEQ ID NO: 1, a heavy chain variable region CDR2 represented by an amino acid sequence of SEQ ID NO: 2, and a heavy chain variable region CDR3 represented by an amino acid sequence of SEQ ID NO: 3.

In another aspect of the present disclosure, the present disclosure provides a light chain variable region of a c-Met-specific antibody including: a light chain variable region CDR1 represented by an amino acid sequence of SEQ ID NO: 4, a light chain variable region CDR2 represented by an amino acid sequence of SEQ ID NO: 5, and a light chain variable region CDR3 represented by an amino acid sequence of SEQ ID NO: 6.

In still another aspect of the present disclosure, the present disclosure provides a c-Met-specific antibody including: a heavy chain variable region of the c-Met-specific antibody including a heavy chain variable region CDR1 represented by an amino acid sequence of SEQ ID NO: 1, a heavy chain variable region CDR2 represented by an amino acid sequence of SEQ ID NO: 2, and a heavy chain variable region CDR3 represented by an amino acid sequence of SEQ ID NO: 3; and a light chain variable region of the c-Met-specific antibody including a light chain variable region CDR1 represented by an amino acid sequence of SEQ ID NO: 4, a light chain variable region CDR2 represented by an amino acid sequence of SEQ ID NO: 5, and a light chain variable region CDR3 represented by an amino acid sequence of SEQ ID NO: 6, or fragments thereof.

Specifically, the present disclosure obtained a fully human antibody bound to c-Met with high affinity and specificity from single-chain Fv(ScFv) phage library by using a phage display method. Phage library and phage display may be prepared by the following known U.S. Pat. No. 7,063,943, U.S. Pat. No. 6,172,197, etc.

The c-Met-specific antibody according to the present disclosure obtained and provided by the method has the heavy chain variable region including the heavy chain variable region CDR1 (HCDR1), the heavy chain variable region CDR2 (HCDR2), and the heavy chain variable region CDR3 (HCDR3) having sequences of SEQ ID NOS: 1, 2 and 3, respectively, and the light chain variable region including the light chain variable region CDR1 (LCDR1), the light chain variable region CDR2 (LCDR2), and the light chain variable region CDR3 (LCDR3) having sequences of SEQ ID NOS: 4, 5 and 6, respectively.

In an exemplary embodiment of the present disclosure, the c-Met-specific antibody according to the present disclosure is 1E4 antibody consisting of a heavy chain variable region having a sequence of SEQ ID NO: 7 and a light chain variable region having a sequence of SEQ ID NO: 8.

Further, the present disclosure provides the heavy chain variable region including HCDR1, HCDR2, and HCDR3 represented by SEQ ID NOS: 1, 2 and 3, respectively, and the light chain variable region including LCDR1, LCDR2, and LCDR3 represented by SEQ ID NOS: 4, 5 and 6, respectively. Preferably, the present disclosure provides the heavy chain variable region represented by SEQ ID NO: 7 of the 1E4 antibody and the light chain variable region represented by SEQ ID NO: 8 of the 1E4 antibody.

TALBLE 1

Sequnces of CDR and variable region of Heavy chain and Light chain of c-Met specific antibody according to the present disclosure

| SEQ ID NO. | Types | Sequences |
|---|---|---|
| 1 | Heavy chain CDR1 (HCDR1) | THWIT |
| 2 | Heavy chain CDR2 (HCDR2) | TIDPTDSYNFYGPSFQG |
| 3 | Heavy chain CDR3 (HCDR3) | DGNYYDSRGYYYDTFDM |
| 4 | Light chain CDR1 (LCDR1) | RASQGISTYLA |
| 5 | Light chain CDR2 (LCDR2) | SASTLES |
| 6 | Light chain CDR3 (LCDR3) | QQADSFPLT |
| 7 | Heavy chain variable region | QVQLVQSGAE VKKPGESLRI SCQGSGYSFP THWITWVRQM PGKGLEWMGT IDPTDSYNFY GPSFQGHVTI SADSSSSTAY LQWSSLKASD TAMYYCARDG NYYDSRGYYY DTFDMWGQGT LVTVSS |
| 8 | Light chain variable region | DIQMTQSPSF LSASVGDRVT ITCRASQGIS TYLAWYQQKP GTAPKLLIYS ASTLESGVPS RFSGSGSGTD FTLTISSLQP EDSATYYCQQ ADSFPLTFGG GTKVEIKRGG ASLVE |
| 9 | Amino acid linker | GLGGLGGGGS GGGGSGGSSG VGS |
| 10 | 1E4 ScFv | QVQLVQSGAE VKKPGESLRI SCQGSGYSFP THWITWVRQM PGKGLEWMGT IDPTDSYNFY GPSFQGHVTI SADSSSSTAY LQWSSLKASD TAMYYCARDG NYYDSRGYYY DTFDMWGQGT LVTVSSGLGG LGGGGSGGGG SGGSSGVGSD IQMTQSPSFL SASVGDRVTI TCRASQGIST YLAWYQQKPG TAPKLLIYSA STLESGVPSR FSGSGSGTDF TLTISSLQPE DSATYYCQQA DSFPLTFGGG TKVEIKRGGA SLVE |

The fragment of the antibody according to the present disclosure as described above is usable with the same purpose. The fragment of the antibody of the present disclosure includes single chain antibodies, diabodies, triabodies, tetra bodies, Fab fragments, F(ab')2 fragments, Fd, ScFv, domain antibodies, bispecific antibodies, minibodies, scab, IgD antibodies, IgM antibodies, IgG1 antibodies, IgG2 antibodies, IgG3 antibodies, IgG4 antibodies, derivatives of antibody constant region, artificial antibodies based on protein scaffolds, etc. having the binding capacity to c-Met, but the present disclosure is not limited thereof. It is obvious to a person skilled in the art that the fragment of the antibody according to the present disclosure also has the same characteristics as the antibody according to the present disclosure as long as the binding function to c-Met is maintained.

The antibody fragment according to the present disclosure may be produced by cutting the entire antibody or expressing DNA encoding the fragment. The antibody fragment may be produced by the method as described in the known document (Lamoyi et al., J. Immunol. Methods, 56: 235, 1983; Parham, J. Immunol., 131: 2895, 1983).

In ScFv in the present disclosure, the heavy chain variable region and the light chain variable region sequences may be linked with each other through a linker, wherein the linker is preferably an amino acid linker, and the amino acid sequence of the linker in ScFv of the 1E4 antibody according to the present disclosure may be a sequence of SEQ ID NO: 9, and all ScFv may be a sequence of SEQ ID NO: 10.

Figure 6:
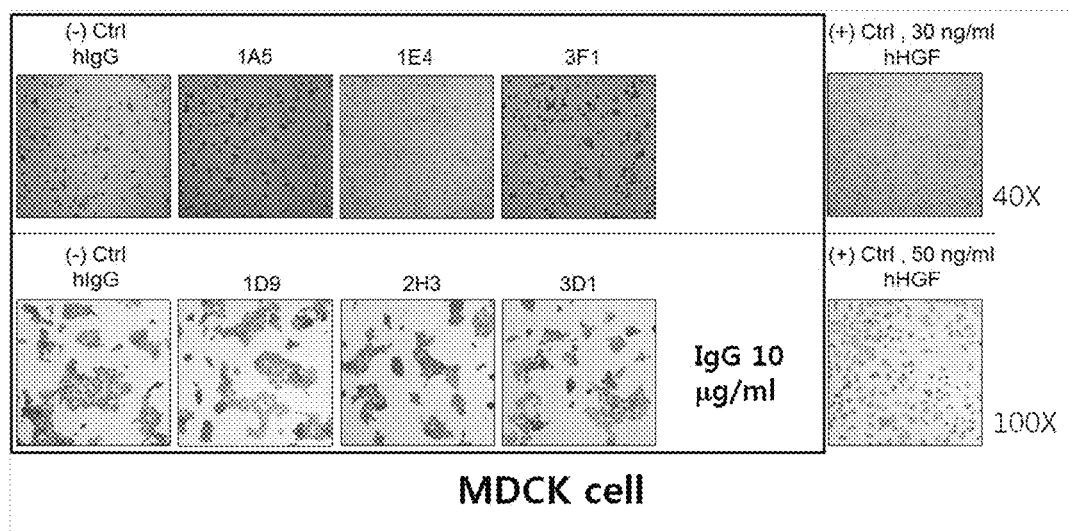
FIG. 6 shows results obtained by confirming scattering of the c-Met-specific antibody according to the present disclosure, through an MDCK-2 cell line.

In an exemplary embodiment of the present disclosure, in the case of 1E4 which is the c-Met-specific human antibody, it was confirmed that c-Met was phosphorylated without treatment of HGF, and as a result obtained by confirming cell scattering by using an MDCK-2 cell which is a dog kidney epithelial cell, the same level of cell scattering as an HGF treated cell group which is a positive control group was confirmed (FIG. 6).

Further, antibodies that are modified in the variable region are also included in the scope of the present disclosure as long as the characteristics of the antibody of the present disclosure are maintained. As an example thereof, conservative substitution of amino acid in the variable region may be included. The conservative substitution means substitution with other amino acid residue having similar characteristics to original amino acid sequence, and for example, lysine, arginine, and histidine have similar characteristics in that they have basic side chains, and aspartic acid and glutamic acid have similar characteristics in that they have acid side chains. Further, glycine, asparagine, glutamine, serine, threonine, tyrosine, cysteine, and tryptophan have similar characteristics in that they have non-charged polar side chains, and alanine, valine, leucine, threonine, isoleucine, proline, phenylalanine, and methionine have similar characteristics in that they have non-polar side chains, and tyrosine, phenylalanine, tryptophan, and histidine have similar characteristics in that they have aromatic side chains. Therefore, it is obvious to a person skilled in the art that even though amino acid substitutions occur in the above-described group having similar characteristics, significant characteristic changes are not shown, such that antibodies that are modified due to conservative substitutions in the variable region are also included within the scope of the present disclosure as long as the characteristics of the antibody of the present disclosure are maintained.

Further, the c-Met-specific antibody according to the present disclosure includes antibodies with improved affinity and specificity by methods such as direct mutation, affinity maturation, phage display, chain-shuffling, etc. Affinity and specificity may be modified or improved by mutating CDR and screening the CDR with respect to antigen-binding sites having desired characteristics (Yang et al., J. Mol. Bio., 254: 392, 1995). The CDR may be mutated in various ways. For example, as one method thereof, development residue or residue combination may be randomized so that all of 20 amino acids are found at specific positions in groups at the same antigen binding sites, and mutants may be induced through over a range of CDR residues by an error prone PCR method causing the mutants (Hawkins et al., J. Mol. Bio., 226: 889, 1992). A phage display vector (phagemid) containing the heavy chain variable region and the light chain variable region gene is reproduced in a mutant strain of $E.$ $coli$ (Low et al., J. Mol. Biol., 250:359, 1996). The mutagenesis method is a method commonly used in the art.

In addition, the antibody according to the present disclosure or fragment thereof is usable in a form of a conjugate that is combined with other materials. Accordingly, the present disclosure provides an antibody-drug conjugate in which the c-Met-specific antibody according to the present disclosure and a therapeutic drug are combined. The therapeutic drug usable for the antibody-drug conjugate according to the present disclosure is usable without limitation as long as it meets the object of the present disclosure.

The present disclosure provides a pharmaceutical composition including the antibody or the fragment thereof according to the present disclosure. The pharmaceutical composition may further include pharmaceutically acceptable conventional carriers, excipients, etc.

In still another aspect, the present disclosure provides a polynucleotide encoding the heavy chain variable region of the c-Met-specific antibody, a recombinant vector containing the polynucleotide, a polynucleotide encoding the light chain variable region of the c-Met-specific antibody, and a recombinant vector containing the polynucleotide.

The polynucleotide sequence encoding the variable region of the antibody or the fragment thereof according to the present disclosure preferably has a heavy chain variable region of SEQ ID NO: 11 and a light chain variable region of SEQ ID NO: 12, but the present disclosure is not limited thereto. Further, it is obvious to a person skilled in the art to which the present disclosure pertains (hereinafter, referred to as a person skilled in the art) that it is possible to have a degenerate sequence, that is, a sequence encoding the same amino acid sequence as the amino acid sequence of the heavy chain variable region represented by SEQ ID NO: 7 and the light chain variable region represented by SEQ ID NO: 8, but having different polynucleotide sequence, and the polynucleotide sequence encoding CDR sequence of each of the heavy chain and the light chain provided by the present disclosure is also capable of being apparently deduced from respective CDR sequences represented by SEQ ID NOS: 1 to 6 by a person skilled in the art.

TABLE 2

Polynucleotide sequence encoding variable region of c-Met specific antibody according to the present disclosure

| SEQ NO. | ID Types | Sequences |
|---|---|---|
| 11 | Heavy chain variable region | caggtgcagc tggtgcagtc tggagcagag gtgaaaaagc ccggggagtc tctgaggatc tcctgtcagg gttctggata cagttttccc acccactgga tcacctgggt gcgccagatg cccgggaaag gcctggagtg gatgggaacg attgatccta ctgactctta caatttctat ggaccgtcgt tccaaggcca cgtcaccatc tcagccgaca gctccagcag caccgcctac ctgcagtgga gcagcctgaa ggcctcggac accgccatgt attactgtgc gagagatggc aactactatg atagtcgcgg ttattactac gatacttttg atatgtgggg ccaagggaca ctggtcaccg tctcctca |
| 12 | Light chain variable region | tccgacatcc agatgaccca gtctccatcc ttcctctctg catctgtcgg agacagagtc accatcactt gccgggccag tcagggcatc agtacttatt tagcctggta tcaacaaaaa ccagggacag cccctaaact cctgatctat tctgcatcca ctttggaaag tggggtccca tcgcgattca gcggaagtgg atccgggaca gatttcactc tcaccatcag cagcctgcag cctgaagatt ctgcaactta ctattgtcaa caggctgaca gtttcccgct cactttcggc ggagggacca aggtggagat caaacgtgga ggagccagcc tcgtggaa |

The present disclosure provides a recombinant vector containing the polynucleotide sequence, a host cell including the same, and a method of producing the antibody specifically bound to c-Met (c-Met-specific antibody) of the present disclosure by using the recombinant vector or the host cell. In particular, the c-Met-specific antibody of the present disclosure is preferably produced by including expression and purification processes in a gene recombinant method, and specifically, is preferably produced by separately expressing each of the variable regions encoding the c-Met-specific antibody of the present disclosure, or by simultaneously expressing the variable regions encoding the c-Met-specific antibody of the present disclosure in one host cell. In addition, polynucleotide encoding a leader sequence is allowed to be positioned at the N-terminal of the antibody of the present disclosure, which is usable in production of the antibody according to the present disclosure. Further, in order to facilitate separation and purification, and analysis of the produced antibody, a tag may be attached. A his-tag is a representative tag, but the present disclosure is not limited thereto.

A term: "recombinant vector" in the present disclosure is an expression vector capable of expressing a target protein in an appropriate host cell, and indicates a gene construct including essential controlling elements operably linked to each other so as to express gene inserts.

A term: "operably linked" in the present disclosure means that nucleic acid expression control sequences and nucleic acid sequences encoding desired protein are functionally linked to each other so as to perform general functions. An operable link with the recombinant vector may be conducted by using gene recombinant technologies well known in the art, and site-specific DNA cleavage and linkage may be easily conducted by using enzymes generally known in the art.

Appropriate expression vectors of the present disclosure may include signal sequences for membrane targeting or secretion in addition to a promoter, an initiation codon, a termination codon, and expression control elements such as polyadenylation signal and an enhancer. The initiation codon and the termination codon are generally considered as portions of nucleotide sequences encoding an immunological target protein, and when a gene construct is administered, the function should be exhibited in an injected subject and should be present in frame with the coding sequences. A general promoter may be constitutive or inducible. Prokaryotic cells have lac, tac, T3 and T7 promoters, but the present disclosure is not limited thereto. Eukaryotic cells have monkey virus 40 (SV40) promoter, mouse mammary tumor virus (MMTV) promoter, human immunodeficiency virus (HIV), for example, HIV long terminal repeats (LTR) promoter, Moloney virus, cytomegalovirus (CMV), Epstein-Barr virus (EBV), rous sarcoma virus (RSV) promoter, and also have β-actin promoter, human hemoglobin-, human muscle creatine-, human metallothionein-derived promoters, but the present disclosure is not limited thereto.

The expression vector may include a selective marker for selecting a host cell containing a vector. The selective marker is to screen a cell transformed with the vector, wherein markers providing a selectable marker phenotype such as drug resistance, auxotrophy, resistance to a cytotoxic agent, or expression of a surface protein may be used Since only cells expressing the selectable marker survive in the environment treated with the selective agent, the transformed cell is possible to be selected. In addition, in the case in which the vector is a replicable expression vector, the vector may include a replication origin which is a specific nucleic acid sequence initiating replication.

As a recombinant expression vector for inserting foreign genes, various vectors such as plasmid, virus, cosmid vector, and the like, may be used. The recombinant vector is not specifically limited in view of kinds as long as it expresses desired gene in various host cells of prokaryotic cells and eukaryotic cells, and produces desired proteins, but a vector capable of producing a large amount of foreign proteins retaining a strong expression with a promoter having strong activity and having similar form to a natural state, is preferred.

In order to express a dual target antibody according to the present disclosure, various expression host/vector combinations may be used. Examples of an expression vector appropriate for an eukaryotic host include expression control sequences derived from SV40, bovine papilloma virus, adenovirus, adeno-associated virus, cytomegalovirus, baculovirus, and retrovirus, but the present disclosure is not limited thereto.

Examples of an expression vector capable of being used in a bacterial host include bacterial plasmids obtained from *Escherichia coli*, such as pET, pRSET, pBluescript, pGEX2T, pUC vector, col E1, pCR1, pBR322, pMB9, and derivatives thereof, plasmid having a larger range of host, such as RP4, phage DNA exemplified as significantly various phage lambda derivatives, such as λgt10 and λgt11, NM989, and other DNA phages such as M13 and filamentous single stranded DNA phage. In particular, for expression in *E. coli*, DNA sequence encoding an anthranilate synthase (TrpE) and a polylinker at carboxy terminal may be included, and other expression vector systems are based on beta-galactosidase (pEX); lambda PL maltose binding protein (pMAL); and glutathione S-transferase (pGST) (Gene 67:31, 1988; Peptide Research 3:167, 1990).

When it is required to perform expression in yeast, a gene appropriately selected for being used in yeast is trpl gene present in the yeast plasmid Yrp7 (Stinchcomb et al., Nature, 282: 39, 1979; Kingsman et al, gene, 7: 141, 1979). The trpl gene provides a selection marker for a mutant strain of yeast that lacks a growing ability in tryptophan, such as ATCC No. 44076 or PEP4-1 (Jones, Genetics, 85: 12, 1977). Accordingly, the presence of trpl damage in the yeast host cell genome provides an effective environment for detecting transformation by growth in the absence of tryptophan. Similarly, leu2-defective yeast strain (ATCC No. 20,622 or No. 38,626) is complemented by known plasmids containing Leu2 gene. The expression vector useful in the yeast cell is 2μ plasmid and derivatives thereof, and a vector useful in an insect cell is pVL941.

The expression vector of the present disclosure may include one or more expression control sequences that are operably linked to a DNA sequence to be expressed or fragments thereof. The expression control sequences are inserted into the vector in order to regulate or control the expression of the DNA sequence to be cloned. Examples of useful expression control sequences may include lac system, trp system, tac system, trc system, major operator and promoter regions of phage lambda, control regions of fd coat protein, a glycolytic promoter of yeast such as a promoter of 3-phosphoglycerate kinase, a promoter of yeast acid phosphatase such as a promoter of Pho5 and yeast alpha-mating factor and promoters derived from polyomavirus, adenovirus, retrovirus, and simian virus such as early and late promoter of SV40, and other sequences known to control gene expression of prokaryotic cells or eukaryotic cells and viruses thereof, and combinations thereof.

In still another aspect, the present disclosure relates to a recombinant cell transformed with the recombinant vector.

In the present disclosure, the recombinant cell is a cell transformed with a recombinant vector containing polynucleotide encoding the heavy chain variable region of the c-Met-specific antibody and a recombinant vector containing polynucleotide encoding the light chain variable region of the c-Met-specific antibody.

In still another aspect, the present disclosure provides a method of producing the c-Met-specific antibody using the recombinant cell, or the fragment thereof, wherein the method including culturing the recombinant cell and separating the c-Met-specific antibody from the cultured recombinant cell.

Preferably, the c-Met-specific antibody according to the present disclosure is preferably obtained by expression and purification according to a gene recombination method. Specifically, the gene sequence encoding the heavy chain variable region or the entire heavy chain region of the antibody and the gene sequence encoding the light chain variable region or the entire light chain region may be expressed in one vector or two vectors, respectively, but the present disclosure is not limited thereto.

Specifically, the method of producing the c-Met-specific antibody may include: producing a recombinant vector by inserting a nucleotide sequence encoding the c-Met-specific antibody of the present disclosure into a vector; transforming and culturing the recombinant vector into a host cell; and separating and purifying the c-Met-specific antibody from the cultured transformant.

In addition, the c-Met-specific antibody may be mass-produced by culturing the transformant in a nutrient medium, the transformant having the recombinant vector expressed therein, wherein medium and culturing condition may be appropriately selected and used depending on host cells. Conditions such as temperature, pH of medium, culturing time, and the like, may be appropriately controlled so as to be appropriate for cell growth and mass-production of protein at the time of culturing.

The c-Met-specific antibody that is recombinantly produced as described above may be recovered from medium or cell lysates. In the case of a membrane-coupled type, the membrane may be isolated by using an appropriate surfactant solution (for example: tritone-X 100) or enzymatic cleavage. Cells used in expressing the c-Met-specific antibody may be destroyed by various physical or chemical means such as freeze-thaw purification, sonic treatment, mechanical damage and cell decomposing agent, and may be isolated and purified by general biochemical isolation technology (Sambrook et al., Molecular Cloning: A Laboratory Manual, 2nd Ed., Cold Spring Harbor Laboratory Press (1989); Deuscher, M., Guide to Protein Purification Methods Enzymology, Vol. 182. Academic Press. Inc., San Diego, Calif. (1990)). Electrophoresis, centrifugation, gel filtration, precipitation, dialysis, chromatography (ion exchange chromatography, affinity chromatography, immunosorbent chromatography, size exclusion chromatography, and the like), isoelectric focusing, and various changes and complex methods are available, but the present disclosure is not limited thereto.

Hereinafter, the present disclosure will be described in more detail with reference to the following Examples. However, the following Examples are only for exemplifying the present invention and it will be obvious to those skilled in the art that the scope of the present invention is not construed to be limited to these Examples.

Example 1: Biopanning

A fully human non-immune single chain antibody (ScFv) phage display library used in biopanning was a phage display library established in the previously registered patent (Korea Patent No. 10-0883430). In order to recover the phage in which the single chain is displayed, a phage library stock solution was grown up to log phase, and rescued by M13K07 helper phage (GE Healthcare, USA), and then amplified overnight by adding 1 mM IPTG to 2×YT medium (2×YT/Cm+, Kan+) containing 34 μg/ml of chloramphenicol (Cm) and 70 μg/ml of kanamycin (Kan) at 30° C.

The phage showing the anti-human Fc ScFv was removed by using human Fc. In order to block other non-specific bindings, phage preparations were allowed to be precipitated in 4% PEG6000/0.5 M NaCl, and re-suspended in 2% skim milk/PBS containing 500 μg/ml of human Fc protein, followed by incubation at 37° C. for 1 hour.

96 well NUNC-IMMUNO plate (Nunc, Denmark) coated with 5 μg/ml of c-Met-Fc (R&D systems, Recombinant human HGF R/c-Met Fc chimera (cat no. 358-MT/CF)) was firstly blocked with 2% skim milk/PBS for 2 hours at room temperature, and 3×10¹¹ pfu of the phage preparation was inoculated at room temperature for 1 hour. The tube was washed with PBST (PBS containing 0.1% Tween 20) five times and then washed with PBS five times. The phage for combination was eluted by using 100 mM triethylamine solution for 10 minutes at room temperature. The eluted phage was maintained together with 10 ml of mid-log phased XL1-Blue cells at 37° C. for 30 minutes, and cultured with shaking for 30 minutes. Then, the infected XL1-Blue cells were cultured overnight at 30° C. in 2×YT/Cm+ plate containing 1% glucose. After first biopanning, second, third, and fourth biopanning were practiced by sequentially increasing the number of washing processes to be 10 times, 15 times, and 20 times, respectively. After fourth panning was practiced, a binding capacity to c-Met of the secured phage was confirmed again through c-Met binding assay.

For performing the c-Met binding assay, a microplate coated with 100 ng of c-Met (R&D system) overnight reacted with 2% skim milk/PBS at 37° C. for 2 hours. The microplate was washed with PBS, and the phages obtained for each panning reacted at room temperature for 1 hour. The reaction solution was washed with PBS, and HRP (Horse radish peroxidase) conjugated mouse anti-M13 antibody (GE healthcare) reacted at room temperature for 1 hour. After the reaction was completed, color-development of the well was induced by using a TMB solution (BD) and absorbance was measured at 450 nm (FIG. 1).

As a result, it was confirmed that 1E4, 1A5, 1D9, 2H3, 3D1 and 3F1 had a binding capacity to c-Met.

Example 2: Production and Purification of Soluble ScFv

In order to manufacture soluble 1E4-ScFv, 1A5-ScFv, 1D9-ScFv, 2H3-ScFv, 3D1-ScFv and 3F1-ScFv with respect to 1E4-ScFv, 1A5-ScFv, 1D9-ScFv, 2H3-ScFv, 3D1-ScFv and 3F1-ScFv confirmed to have the binding capacity to c-Met in Example 1, pET21b-1E4, pET21b-1A5, pET21b-1D9, pET21b-2H3, pET21b-3D1 and pET21b-3F1 were produced by cutting pAK-1E4, pAK-1A5, pAK-1D9, pAK-2H3, pAK-3D1 and pAK-3F1 secured through biopanning with XbaI and EcoRI to secure fragment having 1E4-ScFv, 1A5-ScFv, 1D9-ScFv, 2H3-ScFv, 3D1-ScFv and 3F1-ScFv sequences, and inserting the fragment into an *E. coli* expression vector secured by using the same restriction enzyme (pET21b-6A6, Novagen, U.S.A.). The produced pET21b-1E4, pET21b-1A5, pET21b-1D9, pET21b-2H3, pET21b-3D1 and pET21b-3F1 were transformed into *E. coli* BL21 (DE3) for protein expression, and the soluble ScFv protein was expressed through the transformants, and cells were centrifuged. Then, periplasmic fraction of the cell was secured by using 50 mM Tris (pH 8.0) solution containing 20% sucrose, 200 μg/ml of lysozyme and protease inhibitor cocktail (Roche, Switzerland). The secured fraction was treated by Ni-NTA spin Kit (QIAGEN, Germany) to purify ScFv protein.

Example 3: c-Met Binding Assay Using ScFv

Whether the soluble 1E4-ScFv, 1A5-ScFv, 1D9-ScFv, 2H3-ScFv, 3D1-ScFv and 3F1-ScFv purified in Example 2 had the binding capacity to c-Met, was confirmed. For confirmation, c-Met 100 ng was coated in 96 well NUNC-IMMUNO plate (Nunc, Denmark) at 4° C. overnight, followed by reaction with 2% skim milk/PBS at 37° C. for 2 hours. After the reaction was completed, the plate was washed with PBS, and purified ScFv was added thereto, followed by reaction at room temperature for 1 hour. After the reaction was completed, the plate was washed with PBS, and HRP conjugated anti-Myc mouse antibody (Sigma, USA) was added and reacted at room temperature for 1 hour. Then, the product reacted with TMB solution, and absorbance was measured at 450 nm.

Figure 2:
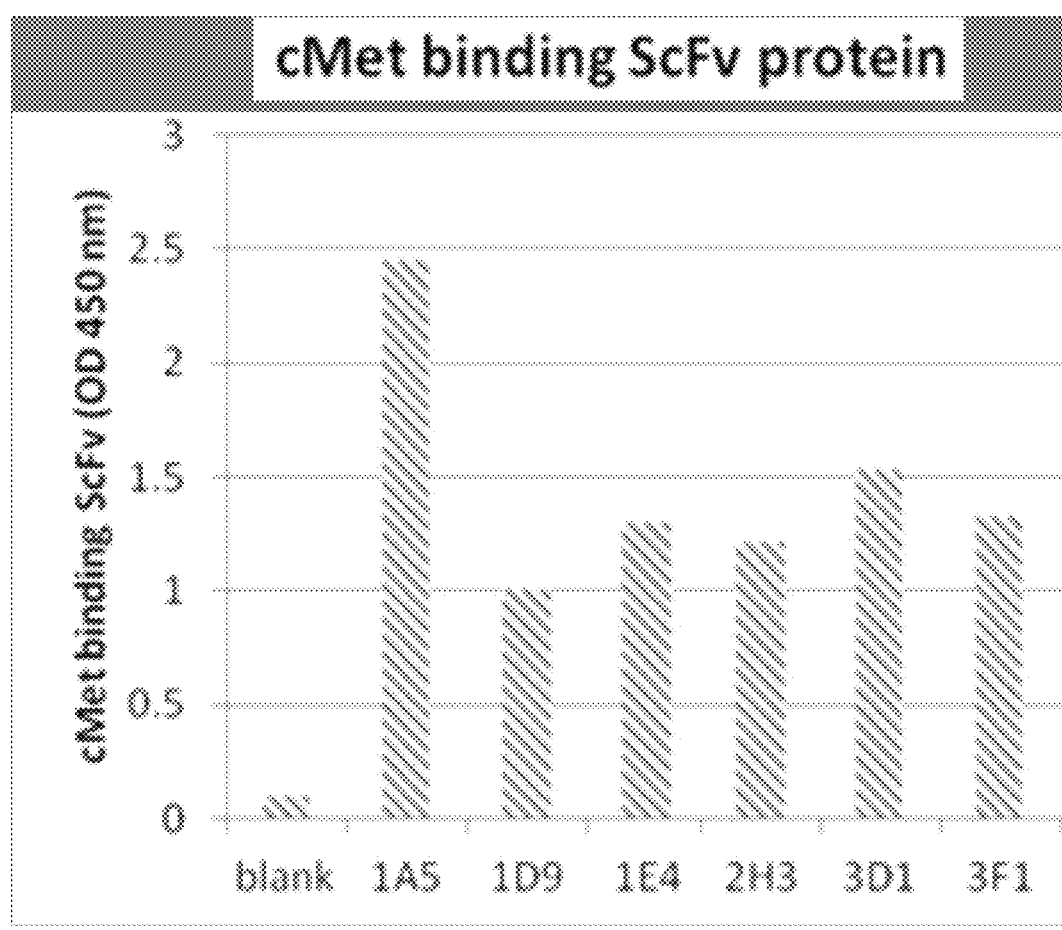
FIG. 2 shows a binding capacity to c-Met, of 1E4-ScFv according to the present disclosure.

As a result, as shown in FIG. 2, it was confirmed that all of the purified 1E4-ScFv, 1A5-ScFv, 1D9-ScFv, 2H3-ScFv, 3D1-ScFv and 3F1-ScFv had the binding capacity to c-Met.

Example 4: Expression and Purification of IgG

Figure 3:
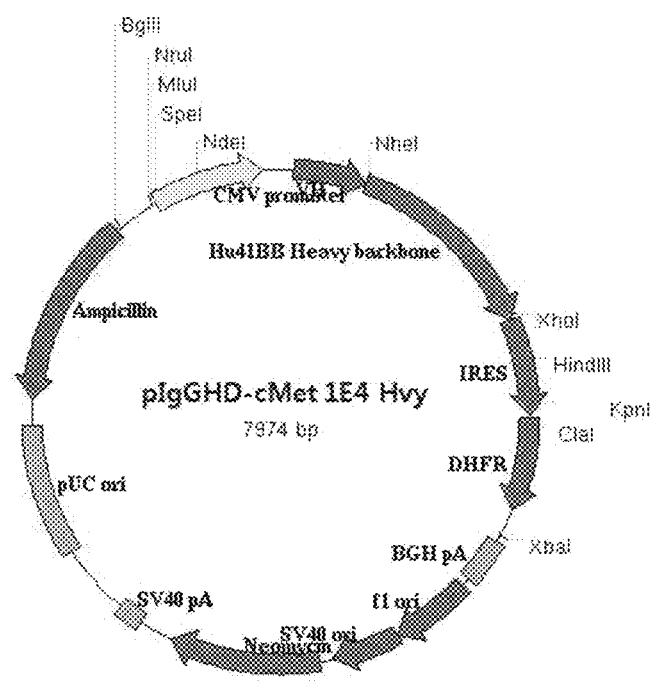
FIG. 3 shows a map of pIgGHD-1E4Hvy which is a vector including a heavy chain constant region and a heavy chain variable region of 1E4-IgG.

In order to be expressed into the entire IgG form, a heavy chain expression vector and a light chain expression vector including the entire constant region were produced. For the heavy chain, pIgGHD-1E4Hvy, pIgGHD-1A5Hvy, pIgGHD-1D9Hvy, pIgGHD-2H3Hvy, pIgGHD-3D1Hvy and pIgGHD-3F1Hvy which are expression vectors including the entire heavy chain constant region and the heavy chain variable region were produced by lygation with a fragment obtained by treating a pIgGHD vector (Aprogen, Korea) having heavy chain backbone of human 4-1 bb with SfiI, and treating a heavy chain variable region of pAKScFv with SfiI (FIG. 3).

Figure 4:
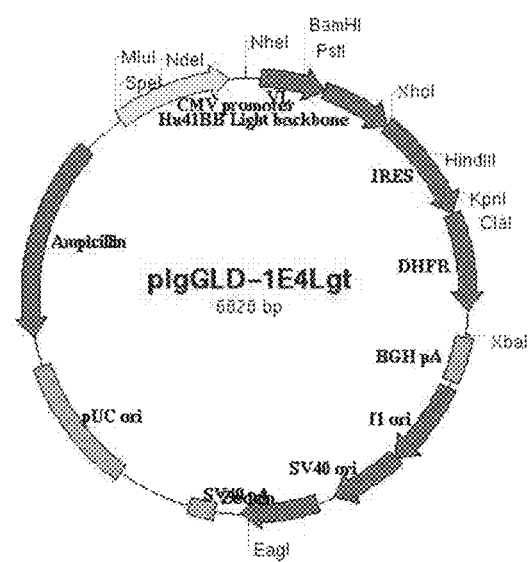
FIG. 4 shows a map of pIgGLD-1E4Lgt which is a vector including a light chain constant region and a light chain variable region of 1E4-IgG.

For the light chain, pIgGLD-1E4Lgt, pIgGLD-1A5Lgt, pIgGLD-1D9Lgt, pIgGLD-2H3Lgt, pIgGLD-3D1Lgt and pIgGLD-3F1Lgt which are expression vectors including the entire light chain constant region and the light chain variable region were produced by lygation with a fragment obtained by treating a pIgGLD vector (Aprogen, Korea) having light chain backbone of human 4-1 bb with BstXI, and treating a light chain variable region of pAK-ScFv with BstXI (FIG. 4).

Figure 5:
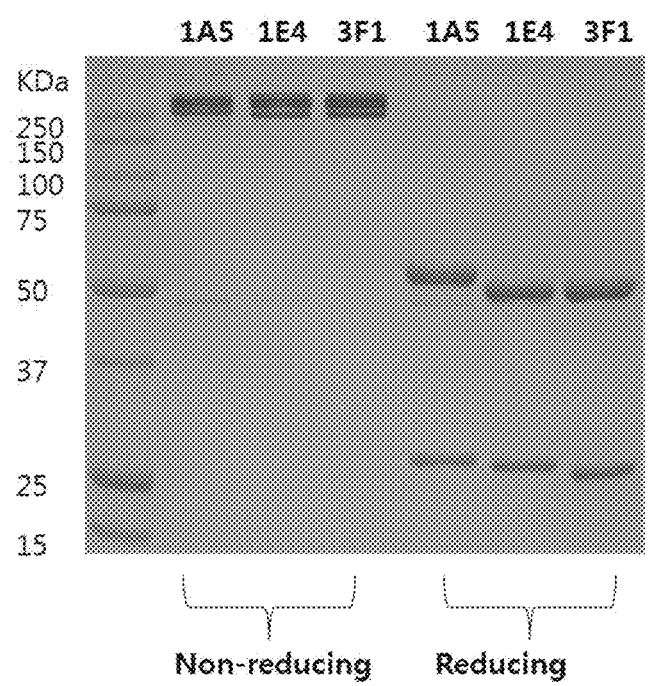
FIG. 5 shows SDS-PAGE results of purified 1E4-IgG.

For IgG expression, the same amount of light chain expression vector and heavy chain expression vector were co-transfected in HEK-293T cell. The transfected cells were cultured in serum free medium Free style 293 (37° C., 5% $CO_2$), and then medium was collected. According to the protocol described by the manufacturer, 1E4-IgG, 1A5-IgG, 1D9-IgG, 2H3-IgG, 3D1-IgG and 3F1-IgG were purified from the supernatant combined through affinity chromatography by using a protein A column (GE Healthcare, USA). The supernatant was injected into the protein A column equilibrated with 20 mM sodium phosphate (pH 7.0) and 100 mM NaCl solution, and washed with 20 mM sodium phosphate (pH 7.0) and a solution containing 1 mM EDTA and 500 mM NaCl, and then eluted with 0.1 M Glycine-HCl (pH 3.3) solution containing 100 mM NaCl. The eluted protein was neutralized with 1M Tris. The eluted protein was mixed with 5 mM sodium phosphate (pH 6.0) buffer at a ratio of 1:1, and injected into a prepacked SP-sepharose (GE healthcare) column that was equilibrated with 5 mM sodium phosphate (pH 6.0) containing 50 mM NaCl. The protein bound to the column was eluted with sodium phosphate (pH 7.0) buffer containing 50 mM NaCl and injected into a prepacked Q-sepharose (GE healthcare) equilibrated with an elution buffer, thereby obtaining unbound protein. The obtained protein was concentrated by 30 Kd vivaspin20 (Sartorius) and dialyzed with PBS. SDS-PAGE results of some of the 1E4-IgG, 1A5-IgG, 1D9-IgG, 2H3-IgG, 3D1-IgG and 3F1-IgG proteins purified by the above-described method were shown in FIG. 5.

Example 5: Analysis of Scattering of c-Met-Specific Antibody

In order to evaluate scattering of six kinds of c-Met-specific antibodies, MDCK-2 (Madin-Darby Canine Kidney Epithelial Cells-2) which is a dog kidney epithelial cell, was cultured. The cell was cultured with DMEM to which 5% fetal bovine serum is added, in 24-well plate at a concentration of 2×10⁴ cell/well. After culturing for one day, once the cells were grown while sticking well to the plate, the cells were treated with 10 μg/ml of antibody or 30 ng/ml or 50 ng/ml of HGF. After culturing for 16 hours, scattering and growth of the cells were evaluated by staining with Chrystal violet (Sigma-Aldrich, U.S.A) and taking images (FIG. 6).

As a result, as shown in FIG. 6, it could be confirmed that only in the case of treating 1E4 among the six kinds of antibodies, the cells were scattered and grown, same as the HGF-treated group which is a positive control group.

Example 6: Analysis of c-Met Phosphorylation In Vivo by Western Blotting

In order to re-confirm activity of 1E4 as an agonist shown in Example 5, phosphorylation activities to c-Met, of 1A5 and 1E4 that are c-Met-specific antibodies were measured by Western blotting. HT29 cells which are rectal cancer cell lines over-expressing c-Met, were cultured in a 6-well plate by 2×10⁵ for 24 hours, and treated in serum-free medium for 6 hours under RPMI medium conditions without including fetal bovine serum, and then 10 μg/ml of hIgG and c-Met antibodies were pre-treated for 30 minutes. Then, 30 ng/ml of human HGF was treated in the treatment group for 15 minutes.

For analysis by western blotting, lysis buffer (1% (w/v) SDS, 10 mM Tris (pH 7.4), 1 mM Na3VO4 (sodium orthovanadate), 2 mM EGTA, 2 mM EDTA, 1 mM phenyl-methylsulfonyl fluoride, 1 mM sodium fluoride, and 1× protease inhibitor cocktail (Sigma) were treated to obtain a lysate and the lysate was boiled, followed by centrifugation at 4° C. at 10,000 g for 5 minutes to remove insoluble precipitate. The supernatant was mixed with SDS sample buffer and boiled for 10 minutes to be prepared. SDS-PAGE and Western blotting were performed by methods generally known in the art, and the used samples were provided as follows: 4-20% SDS-polyacrylamide gel (BioRad, U.S.A.), PVDF membrane (Millipore #IPVH00010, U.S.A.), an anti-c-Met antibody (Santa Cruz, U.S.A.) and an anti-phospho-c-Met antibody (Cell Signaling Technology, U.S.A.) as a primary antibody for analyzing c-Met phosphorylation activity; an anti-p-Erk antibody (Cell Signaling Technology, U.S.A.), and an HRP-conjugated goat anti-mouse IgG antibody (Santa Cruz Biotechnology, U.S.A.) and an HRP-conjugated goat anti-rabbit IgG (Cell Signaling technology, U.S.A.) as a secondary antibody bound to the primary antibody for chemiluminescence (FIG. 7).

Figure 7:
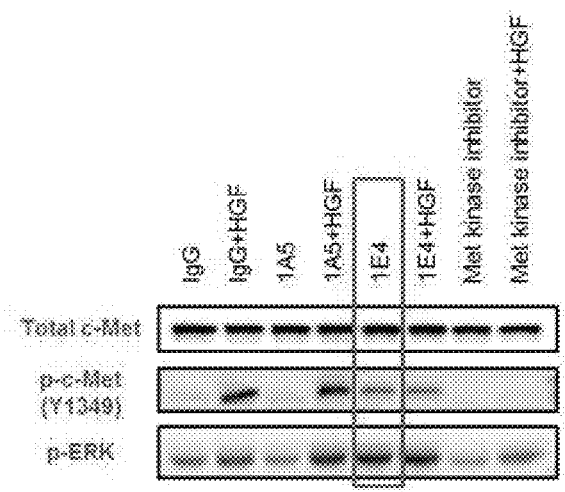
FIG. 7 shows results obtained by confirming a phosphorylation capacity of the c-Met-specific antibody according to the present disclosure, through western blotting.

As a result, as shown in FIG. 7, it could be confirmed that 1E4 had a phosphorylation capacity to c-Met even with a single treatment.

Example 7: Analysis of Binding Capacity of Anti-c-Met IgG (1E4-IgG)

Figure 8:
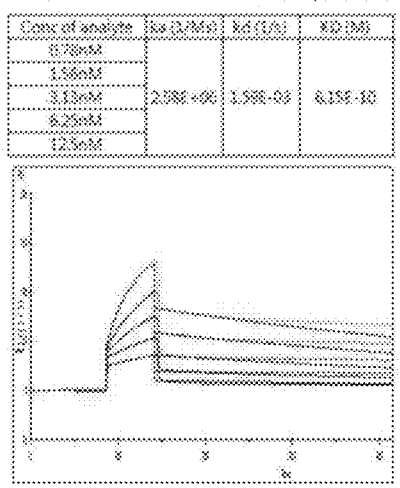
FIG. 8 shows binding capacities to mouse c-Met and to human c-Met, of the c-Met-specific antibody according to the present disclosure.
Figure 8:
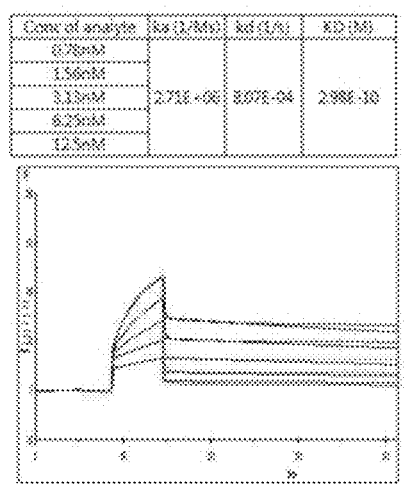

The binding capacity to c-Met of the antibody was measured by a BIACORE® analyzer (GE Healthcare). According to the manufacturer's manual, sensorgrams were secured by immobilizing mouse-c-Met and human-c-Met (R&D system) on a CM5 chip (GE Healthcare, Sweden), and flowing various amounts of antibodies. Rate constants kon and koff were measured on the basis of the sensorgrams secured at each concentration, and Kd was calculated from the ratio of rate constants (koff/kon) (Table 3). As a result, 1E4-IgG had high binding capacity with mouse-c-Met as well as binding capacity with human-c-Met (FIG. 8).

TABLE 3

| ka, kd and Kd value of antibody according to the present invention | | | |
|---|---|---|---|
| | ka (1/Ms) | kd (1/s) | KD (M) |
| mouse c-Met-Fc | $2.58 \times 10^6$ | $1.59 \times 10^{-3}$ | $6.15 \times 10^{-10}$ |
| human c-Met-Fc | $2.71 \times 10^6$ | $8.07 \times 10^{-4}$ | $2.98 \times 10^{-10}$ |

Although specific embodiments of the present invention are described in detail, it will be apparent to those skilled in the art that the specific description is merely desirable exemplary embodiment and should not be construed as limiting the scope of the present invention. Therefore, the substantial scope of the present invention will be defined by the accompanying claims and their equivalents.

INDUSTRIAL APPLICABILITY

The c-Met-specific antibody according to the present invention is capable of specifically binding to c-Met with high affinity and having an agonist function.

The invention claimed is:

1. A c-Met-specific antibody or an antigen binding fragment thereof comprising:
   a heavy chain variable region CDR1 having the amino acid sequence of SEQ ID NO: 1; a heavy chain variable region CDR2 having the amino acid sequence of SEQ ID NO: 2; and a heavy chain variable region CDR3 having the amino acid sequence SEQ ID NO: 3; and
   a light chain variable region CDR1 having the amino acid sequence of SEQ ID NO: 4; a light chain variable region CDR2 having the amino acid sequence of SEQ. ID NO: 5; and a light chain variable region CDR3 having the amino acid sequence of SEQ ID NO: 6.

2. The c-Met-specific antibody or the antigen binding fragment thereof according to claim 1, wherein the heavy chain variable region has the amino acid sequence of SEQ ID NO:7.

3. The c-Met-specific antibody or the antigen binding fragment thereof according to claim 1, wherein the light chain variable region has the amino acid sequence of SEQ ID NO:8.

4. A polynucleotide encoding the c-Met-specific antibody or the antigen binding fragment thereof according to any one of claims 1 to 3.

5. The polynucleotide according to claim 4, comprising the nucleotide sequence of SEQ ID NO: 11 or SEQ ID NO: 12.

6. A recombinant expression vector comprising the polynucleotide encoding the c-Met-specific antibody or the antigen binding fragment thereof according to claim 4.

7. A host cell transformed with the recombinant expression vector according to claim 6.

8. A method of producing a c-Met-specific antibody or an antigen binding fragment thereof according to claim 1 comprising: culturing the host cell according to claim 7, and recovering the c-Met-specific antibody or the antigen binding fragment thereof from the culture.

* * * * *